US007262415B2

(12) United States Patent
Crosetto

(10) Patent No.: US 7,262,415 B2
(45) Date of Patent: Aug. 28, 2007

(54) GANTRY FOR GEOMETRICALLY CONFIGURABLE AND NON-CONFIGURABLE POSITRON EMISSION TOMOGRAPHY DETECTOR ARRAYS

(76) Inventor: Dario B. Crosetto, 900 Hideaway Pl., DeSoto, TX (US) 75115

( * ) Notice: Subject to any disclaimer, the term of this patent is extended or adjusted under 35 U.S.C. 154(b) by 185 days.

(21) Appl. No.: 10/453,255

(22) Filed: Jun. 2, 2003

(65) Prior Publication Data
US 2004/0097800 A1 May 20, 2004

Related U.S. Application Data

(60) Provisional application No. 60/385,140, filed on Jun. 2, 2002.

(51) Int. Cl.
*G01T 1/161* (2006.01)
(52) U.S. Cl. .................. 250/363.05; 250/363.04; 250/363.08
(58) Field of Classification Search .......... 250/363.05, 250/363.04, 363.08
See application file for complete search history.

(56) References Cited

U.S. PATENT DOCUMENTS 5,838,009 A * 11/1998 Plummer et al. ...... 250/363.05
5,937,202 A 8/1999 Crosetto
6,583,420 B1 * 6/2003 Nelson et al. .............. 250/397

FOREIGN PATENT DOCUMENTS

WO WO01/87140 A3 11/2001

OTHER PUBLICATIONS

Brownell, Gordon. "A History of Positron Imaging", presented on Oct. 15, 1999 to the Massachusetts General Hospital.
Crosetto. "400+ times improved PET Efficiency for Lower-Dose Radiation, Lower-Cost Cancer Screening", 3-D Computing, Jun. 30, 2001, ISBN: 0970289707.

* cited by examiner

*Primary Examiner*—David Porta
*Assistant Examiner*—Shun Lee
(74) *Attorney, Agent, or Firm*—Jones Day; Brett Lovejoy

(57) ABSTRACT

A gantry system for geometrically configuring a plurality of detectors for image scanning a patient comprises a plurality of essentially planar sensor support rings forming a barrel surrounding a central scanning area. Each ring is formed by opposing upper and lower semi-elliptical array supports, and each array support is configured to support a plurality of adjustable detector assemblies. Each array support is adjustable along a longitudinal axis of the barrel, and collectively define an imaging field of view that is configurable by separately adjusting one or more of the array supports. Upper array supports are also preferably moveable in a generally perpendicular direction with respect to longitudinal axis, e.g., to optimize position of the detector assemblies with respect to a patient, to provide for easier patient entry and/or to provide for scans of claustrophobic or obese patients.

3 Claims, 11 Drawing Sheets

GANTRY FOR GEOMETRICALLY CONFIGURABLE AND NON-CONFIGURABLE POSITRON EMISSION TOMOGRAPHY DETECTOR ARRAYS

CROSS REFERENCES TO RELATED APPLICATIONS

The present application is related to and claims priority from U.S. Provisional Patent Application 60/385,140 entitled, "Method And Apparatus For A Low-Radiation, Low-Examination Cost, Three-Dimensional Complete Body Screening," filed on Jun. 2, 2002. The above identified application is incorporated by reference herein in its entirety.

BACKGROUND OF THE INVENTION

1. Field of the Invention

The present invention relates to positron emission tomography (PET). More particularly, the present invention relates to an apparatus for providing geometrically configurable mechanical support PET detector arrays.

2. Description of Related Art

Detectors employed for PET scanning (imaging) are relatively small compared to other detectors used for detecting photons. For instance, PET detectors are about 200 times smaller than the large detectors for high-energy physics and require identification of only one type of particles, the photons. The task of capturing and identifying the particles is relatively easier than before: one type of particle instead of five and on a detector 200 times smaller.

The use of positron emissions for medical imaging has been well documented from the early 1950's, see "A History of Positron Imagining," Brownell, Gordon, presented on Oct. 15, 1999, Massachusetts General Hospital and available at http://neurosurgery.mgh.harvard.edu/docs/PEThistory.pdf, which is incorporated herein by reference in its entirety. PET imaging has advantages over other types of imaging procedures. Generally, PET scanning provides a procedure for imaging the chemical functionality of body organs rather than imaging only their physical structure, as is commonly available with other types of imaging procedures such as X-ray, computerized tomography (CT), or magnetic resonance imaging (MRI). PET scanned images allow a physician to examine the functionality of the heart, brain, and other organs as well as to diagnose disease groups which cause changes in the cells of a body organ or in the manner they grow, change, and/or multiply out of control, such as cancers.

Other applications for detecting particles (photons, electrons, hadron, muon and jets) are well known, such as with regard to experiments in high energy physics. While particle detection in high energy physics and medical imaging have some common ground, differences between the disciplines are sticking. One distinction between the usages is that the detectors used in medical imaging are approximately 200 times smaller than the larger detectors employed in high-energy physics applications, and what is more, medical imaging PET applications require the identification of only a single type of particle, the photon.

Typically, prior art PET devices require the injection into the patient's body of a radiation dose that is 10 to 20 times the maximum radiation dose recommended by the International Commission on Radiological Protection (ICRP). This amount is necessary because, at best, prior art PET devices detect only two photons out of 10,000 emitted in the patients' body. Currently the largest manufacturers of PET (General Electric Company and Siemens AG (ADR)) which command in excess of 90% of the world market, are manufacturing two different PET (PET/CT) systems with very similar performance and are selling them at very similar prices. However, although the price and performance of the systems from the different manufactures are comparable, one manufacturer's system (Siemens) uses nearly ideal crystal detectors, while in contrast, the other manufacturer's system (General Electric) uses cheaper, lower quality crystal detectors with slower decay time. Consequently, the manufacturer using the cheaper, lower cost detectors, expends on the order of only 10% the price of the ideal crystals used in their competitor's systems. Thus, the question arises: how it could be that even though one manufacturer uses crystals detectors that are ten times more expensive that the other manufacturer, the price and performance of the two PET systems from the different manufacturers are very comparable.

Anecdotally, the present inventor has analyzed the progress of the most significant PET improvements made in the most recent 17 years, see "400+times improved PET efficiency for lower-dose radiation, lower-cost cancer screening," 3D-Computing, Jun. 30, 2001, ISBN: 0970289707, which is incorporated herein by reference in its entity. The improved PET device is also taught by the present inventor in co-pending U.S. Non-Provisional patent application Ser. No. 10/250,791, entitled "Method And Apparatus For Anatomical And Functional Medical Imaging," relating to and claiming priority from PCT/US01/15671, filed May 15, 2001 which relates to and claims priority from U.S. Provisional Patent Application No. 60/204,900 filed May 16, 2000, U.S. Provisional Patent Application No. 60/215,667 filed Jun. 30, 2000, U.S. Provisional Patent Application No. 60/239,543 filed Oct. 10, 2000, U.S. Provisional Patent Application No. 60/250,615 filed Nov. 30, 2000, U.S. Provisional Patent Application No. 60/258,204 filed Dec. 22, 2000 and U.S. Provisional Patent Application No. 60/261,387 filed Jan. 15, 2000 which are each incorporated herein by reference in their entirety.

Problems inherent in the prior art PET devices include low device efficiency, poor image quality due to, for instance, low spatial resolution, long examination times, and high dosages of radiation to the patient. These shortcomings result in high examinations costs to the patient, prolonged payback of capital and unsuitability of the current PET technology to adapt to well-patient procedures. These shortcomings are described in greater specificity U.S. patent application Ser. No. 10/376,024 filed on Feb. 26, 2003 titled "Method and Apparatus for Determining Depth of Interactions in a Detector for Three-Dimensional Complete Body Scanning" and which is incorporated herein by reference in its entirety.

FIG. 1 is a simplified diagram of a PET device as known in the prior art. Essentially PET scanner 100 provides a plurality of scintillation detector assemblies arranged in a cylindrical geometric configuration as is well known in the prior art. Each detector assembly comprises a crystal 112, and at least one a light amplifier per detector. Crystal 112 might be any type which interacts with a photon so as to produce a scintillation, or rapid flash of light in the interior lattice structure of the crystal. Typically, crystal 112 is optically coupled to one or more optical amplifiers which have a detector integrated therein. Thus, as a practical matter amplifiers 114 may be Photomultipliers (PMTs), Avalanche Photodiodes (APDs) or some other type of light emitting diode, however each amplifier-detector combination will have a signal output (a channel) for outputting the amplified signal to the processing electronics.

As mentioned above, detector array 110 is geometrically configured as an open ended cylinder, having ingress opening 102 and egress opening 104 of sufficient diameter for accepting the cross-sectional diameter of a patient's body. As compared to the height of a human body, the total detector length of array 110 is rather small, typically on the order of 5.9 in. to 9.8 in. (15 cm.-25 cm.). This is known as the field of view (FOV) of the detector array. The reason for the prior art PET devices having very small FOVs is because, among other reasons, the capital expense in the detectors. Even if a PET were configured with a larger FOV, the resulting device would not overcome the shortcoming of the prior art because prior art technologies do not fully exploit the double photon emission phenomenon. Moreover, current PET devices utilized electronics that saturate, even at relatively modest photon capture rates. Thus, any increase in the FOV over which the electronics can process the additional photons are wasted. By way of example, typically prior art PET devices capture on the order of two photons for every 10,000 photons emitted from the patient's body. Thus, it takes approximately 55 minutes to scan 70 cm FOV. Clearly utilizing only two out of every 50,000 photons available drastically reduces the data quality and lower resolution images are the result.

Typically the patient is conveyed along the interior of cylindrical detector array 110 for the device to effectively scan the patient's body. Turning to FIG. 2, a cross-sectional view detector array 110 of PET 100 is depicted. Also show is patient 220, who is oriented substantially coaxial with the FOV of detector array 110. Notice that the cross-sectional view of array 110 depicts the detectors as being configured in a near-perfect circle. This configuration is necessary in order to lessen the effects of parallax errors. A error results from assuming that photons strike the detector at 90 degrees to its face. It is expected that photons enter the crystal following a path which is perpendicular to the face of the crystal and parallel with the length of the detector, i.e., straight into one detector only. When a photon enters the crystal at 90 degrees, its X-Y position can be easily calculated from the detectors which perceive the scintillation effect in the crystal, the X-Y position through a centroid calculation. The depth at which the photon interacts with the crystal is unimportant in this case where the photon penetrates the crystal perpendicular to the face, because it will interact somewhere along a line in oriented in the Z direction formed by the intersection of an X plane and a Y plane, i.e. the line of response (LOR) is found perpendicular to the X-Y planes. This presumes that all lines of response between coincidental pairs of detectors intersect the center point of the barrel.

Given the already low efficiency of the current PET devices, configuring the cross-section of detector array 10 in a circle gives better results because some parallax errors are avoided because a largest proportion of the photons must enter the crystal at 90 degrees from the crystal's face.

This configuration has several undesirable consequences. The first is that array 10 is permanently configured as a circle. Claustrophobic patients must be transported through the interior of the PET for optimal results. Recall that for imaging, a FOV of a mere 27 inches requires that the patient remaining motionless for 55 minutes, which is difficult for patients not suffering from claustrophobia and nearly impossible for those who do suffer from claustrophobia.

Furthermore, notice from FIG. 2, that while the radial displacement of the detectors does reduce parallax error, it cannot be eliminated altogether. The circularly configuration necessarily orients all detectors toward the center point of the circle and therefore handles only photons which are generated along those paths, shown in the figure as photon paths 230. Photons generated in the extremities of the patients body, or those not traveling in pathways 230 may still result in parallax error which will reduce the image quality.

Aside from the cost of large diameter arrays, most facilities simply do not have the vertical clearance for supporting a detector array diameter sufficient for scanning larger individuals. Thus, in addition to those patients suffering from claustrophobia, patients with larger frames and/or obese patients can not be accommodated with current PET technology.

As a final matter, the PET scanning process itself dictates the use of detector array oriented in a circular configuration because the patient's body is transported across the FOV of the detectors rather than being scanned while stationary. Since the cross-section of a patient's body patient continually changes with respect to the array as it passes through, the prior art simply have no alternative but to compromise on circular array configuration for handling any cross-sectional shape. Even with respect to parts of the body where a circular detector array would be most optimal, such as the patient's head, the detector array is situated for the maximum cross-sectional area of the patient, i.e., the torso, and therefore cannot give the best results in more narrow regions of the body.

What is needed is a means for increasing the accuracy and efficiencies of PET devices enabling caregivers to more accurately diagnose aliments related to the functionality of body organs and not just inferences from the structure of the organs. Also, what is needed is a more flexible device which will accommodate more patients, those who suffer from claustrophobia, obesity or who are simply larger individuals. Also what is needed is a geometrical configurable PET for use in research and academia.

SUMMARY OF THE INVENTION

The present invention is directed to a system for geometrically configuring a plurality of detectors for image scanning a patient. The detector barrel of the present gantry system comprises a plurality of essentially planar sensor support rings. Each ring is formed by two semi-elliptical planar support portions, for independent support of detector assemblies or array of detector assemblies. The semi-elliptical planar supports are generally aligned and supported along the longitudinal axis of the barrel, forming two opposing half-barrel shapes. The imaging field of view is configurable by separately adjusting any or all of the semi-elliptical planar supports in either half barrel. One or both half-barrel detector arrays is preferably mobile, capable of being displaced away from the center axis to allow for easier patient entry and/or scans of claustrophobic or obese patients. In addition to the flexibility offered by the semi-elliptical planar supports, each of detector assemblies may be adjustably attached to the planar supports by a separately configurable mounting support for aiming individual detectors or arrays of detectors.

BRIEF DESCRIPTION OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

Other features of the present invention will be apparent from the accompanying drawings and from the following detailed description.

DETAILED DESCRIPTION OF THE INVENTION

Figure 1:
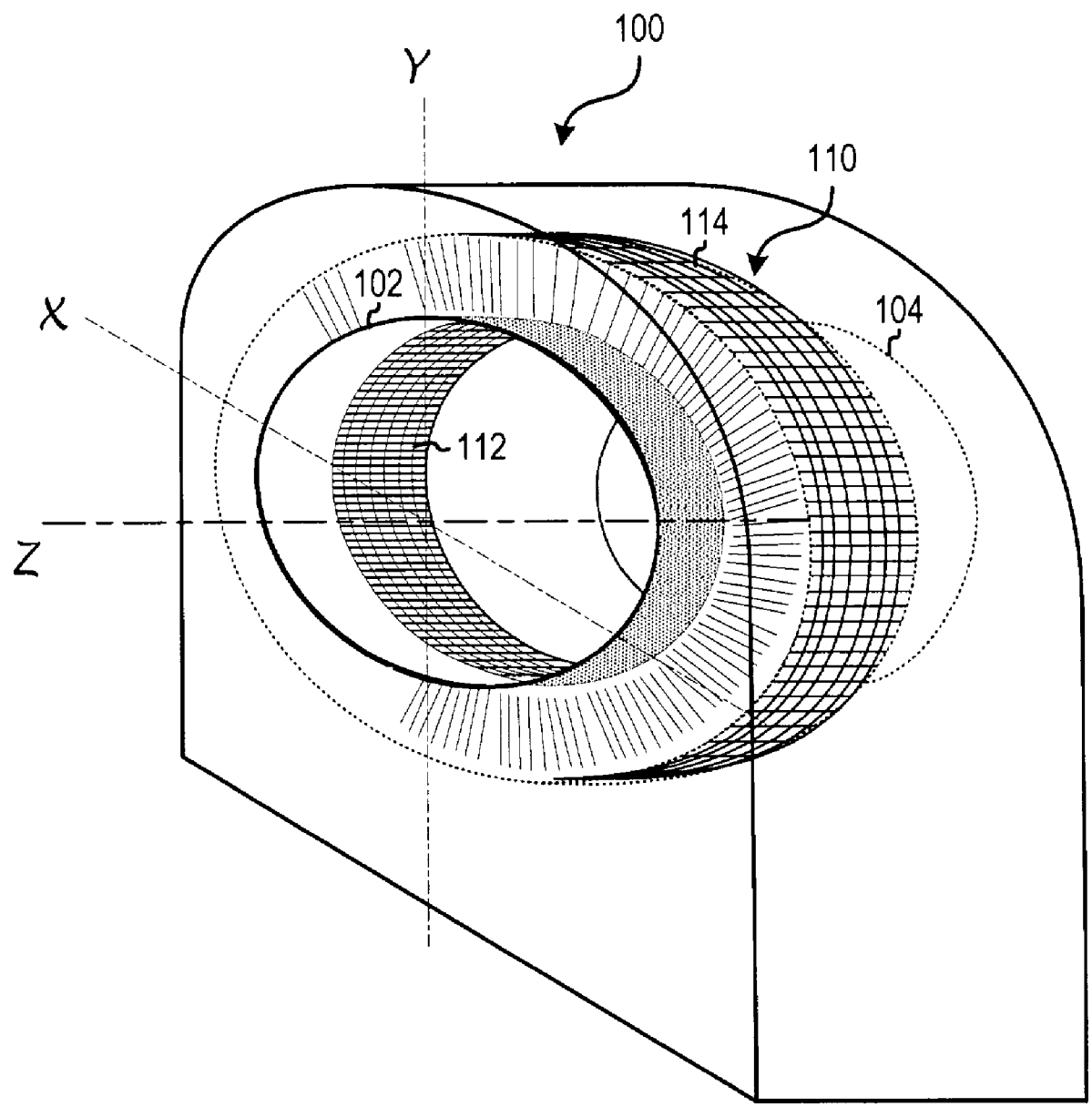
FIG. 1 is a simplified diagram of a PET device as known in the prior art. Essentially PET scanner 100 provides a plurality of scintillation detector assemblies arranged in a cylindrical geometric configuration as is well known in the prior art.
Figure 2:
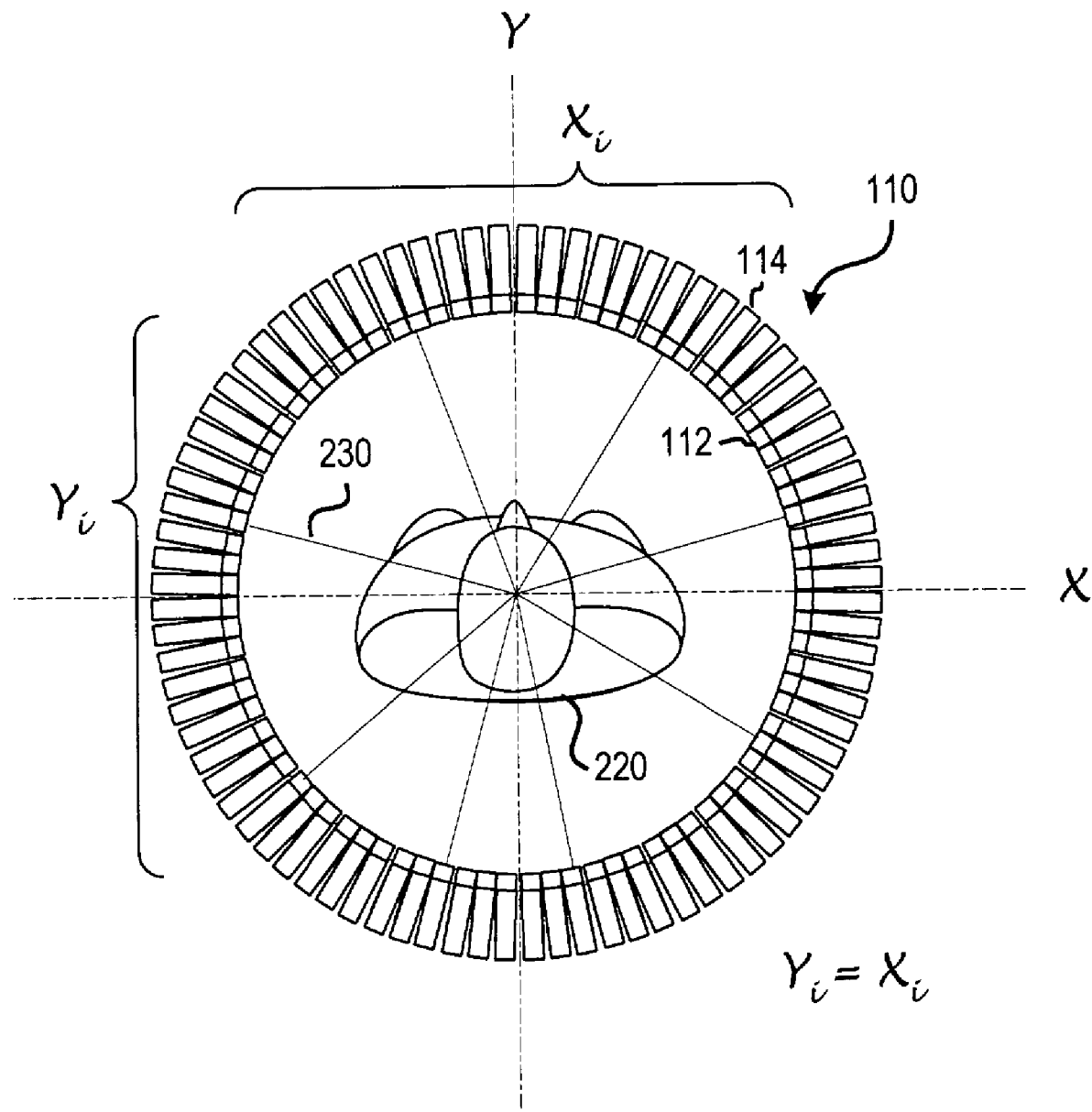
FIG. 2, a cross-sectional view detector array 10 of PET 100 is depicted.
Figure 3:
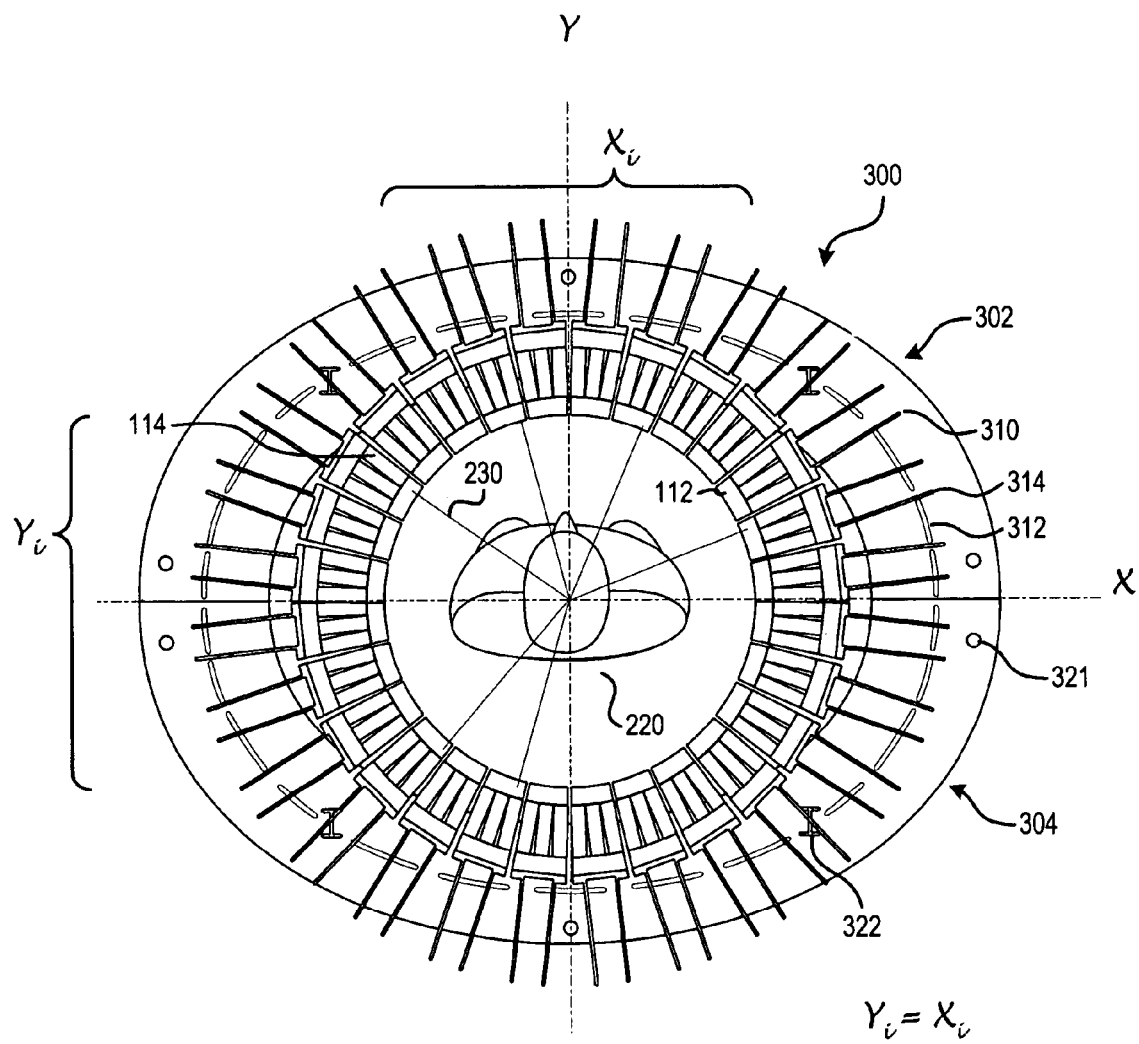
FIG. 3A is a diagram of a cross-sectional area of a geometrically configurable detector array in accordance with an exemplary embodiment of the present invention.
FIG. 3B is a diagram of a cross-sectional area of a geometrically configurable detector in accordance with an exemplary embodiment of the present invention.
Figure 3A:
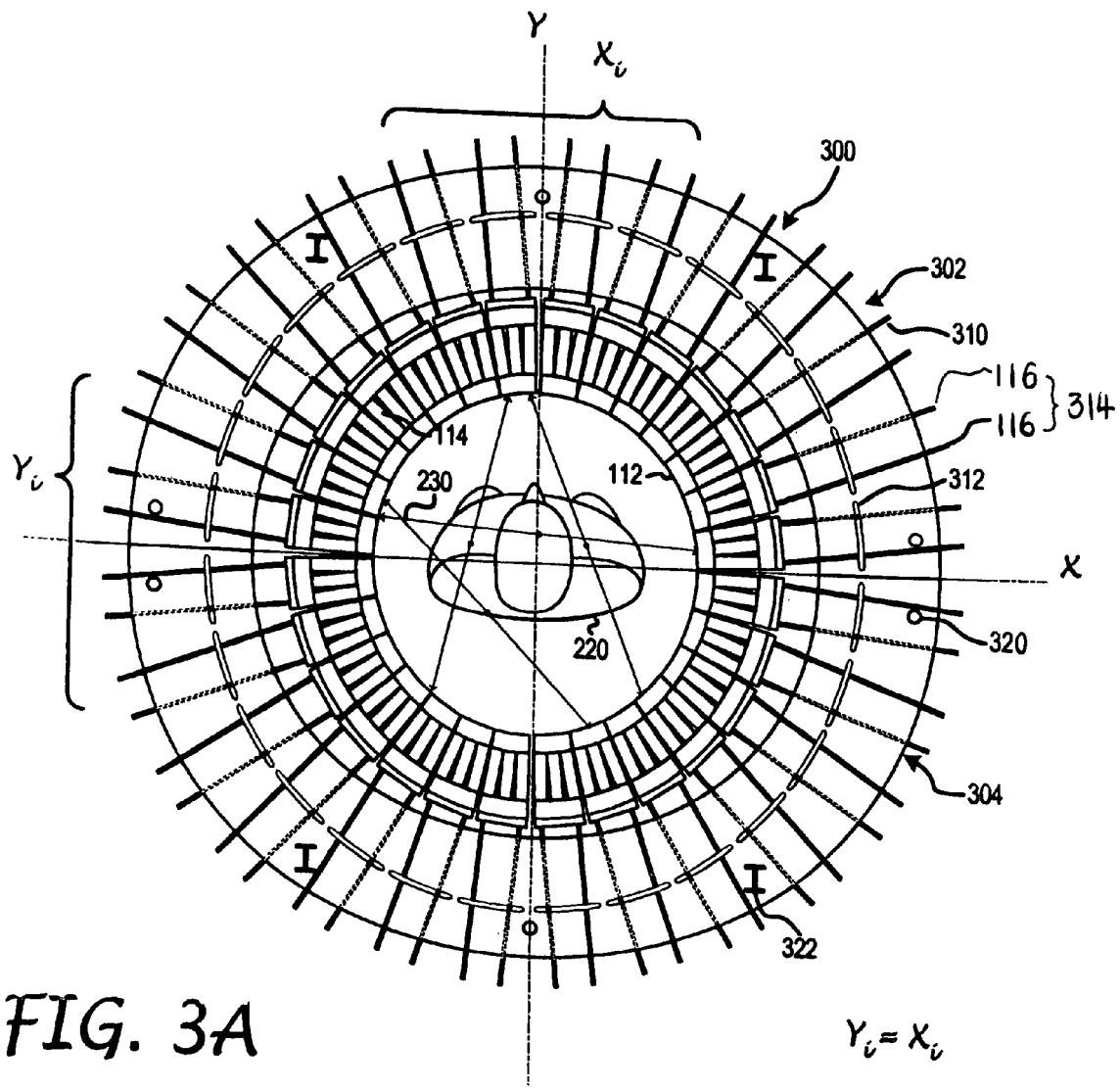

The present invention is directed to a gantry suitable for geometrically configurable and non-configurable positron emission tomography detector arrays. FIG. 3A is a diagram of a cross-sectional area of geometrically configurable detector array in accordance with an exemplary embodiment of the present invention. As will be understood below, the present invention utilizes multiple cross-sectional arrays (FOV arrays), each separately geometrically configurable for a portion of the patient's body. Without elaboration, the present invention is possible because of the extremely high efficient electronics utilized by the 3D-Flow sequentially implemented parallel-processing architecture, described in detail for example in U.S. Non-Provisional patent application Ser. No. 10/250,791, filed on May 15, 2001 and entitled "Method And Apparatus For Anatomical And Functional Medical Imaging," relating to and claiming priority from PCT/US01/15671.

FOV array 300 has a geometrically configurable barrel portion which includes upper array support 302 and lower array support 304. Taken together, upper array support 302 and lower array support 304 form a cross section of the barrel portion the shape of a circle or ellipsis for supporting multiple sets of geometrically configurable detectors. Also shown in the diagram is a plurality of configurable detector assemblies 310, also referred to a detectors 310, including crystal 112, amplifier 114 and attachment means, depicted here as attachment arms 116, but may alternatively be an mechanism for configuring detector assemblies 310 onto one of upper array support 302 and lower array support 304. To that end, notice also that each of upper array support 302 and lower array support 304 has cooperating attachment recesses 312 for accepting fasteners for holding assembly 310. More specifically, mounting support 314 cooperates with cooperating attachment recesses 312. In addition, each of upper array support 302 and lower array support 304 has one or more means for accepting a load-bearing member, I-beam slots 322 and for cooperating with an alignment stability member, holes 321. Clearly, these accommodations are merely representative and one of ordinary skill level in the relevant art would readily adapt other mechanism for providing mechanical support, structural integrity and for configuring the geometry of the array. Essentially, each of upper array support 302 and lower array support 304 forms a semi-elliptical or arc shaped platform which provides the mechanical integrity necessary for supporting the detector array and transmitting the weight to load-bearing structures on the gantry.

Figure 3B:
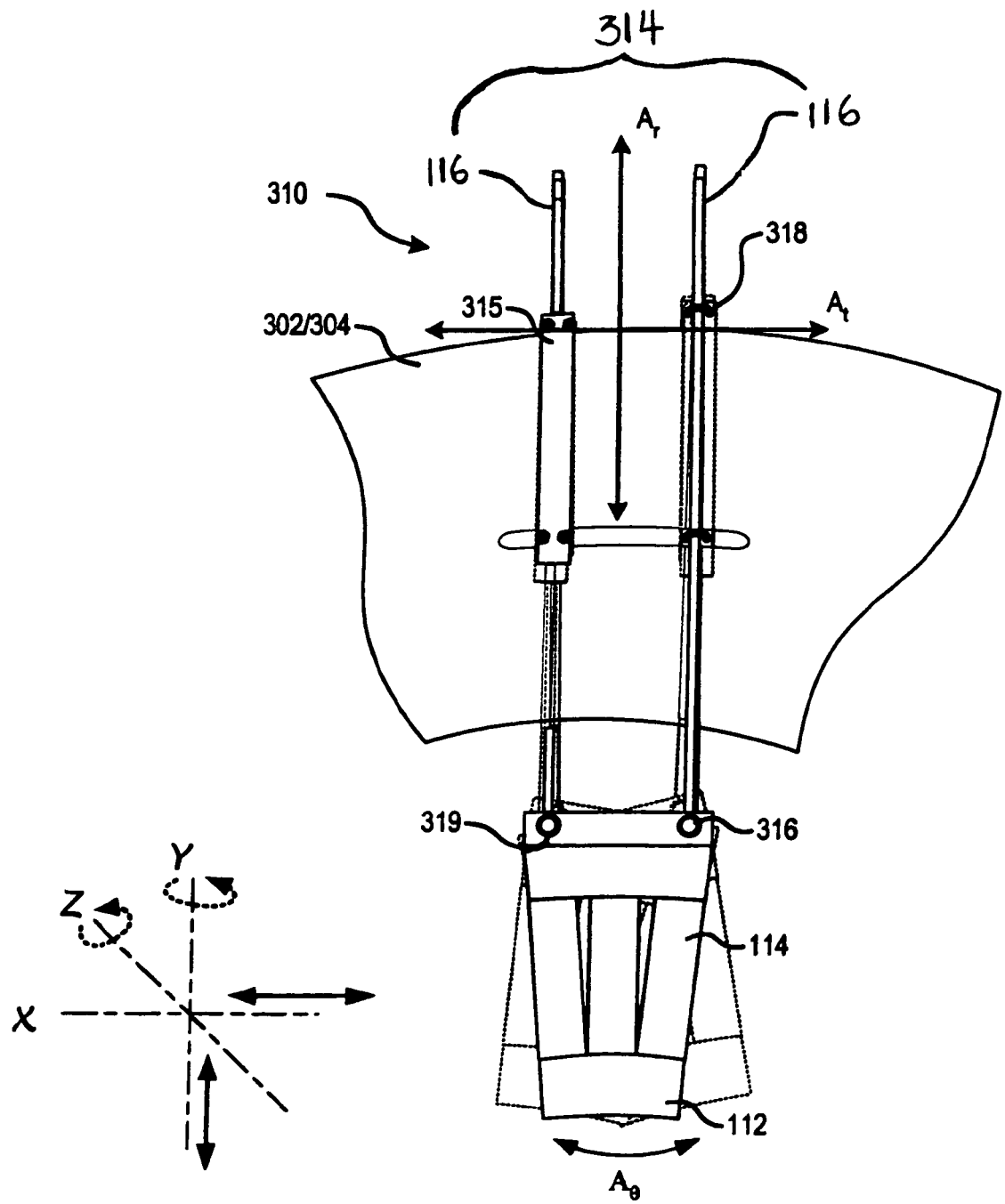
Figure 4:
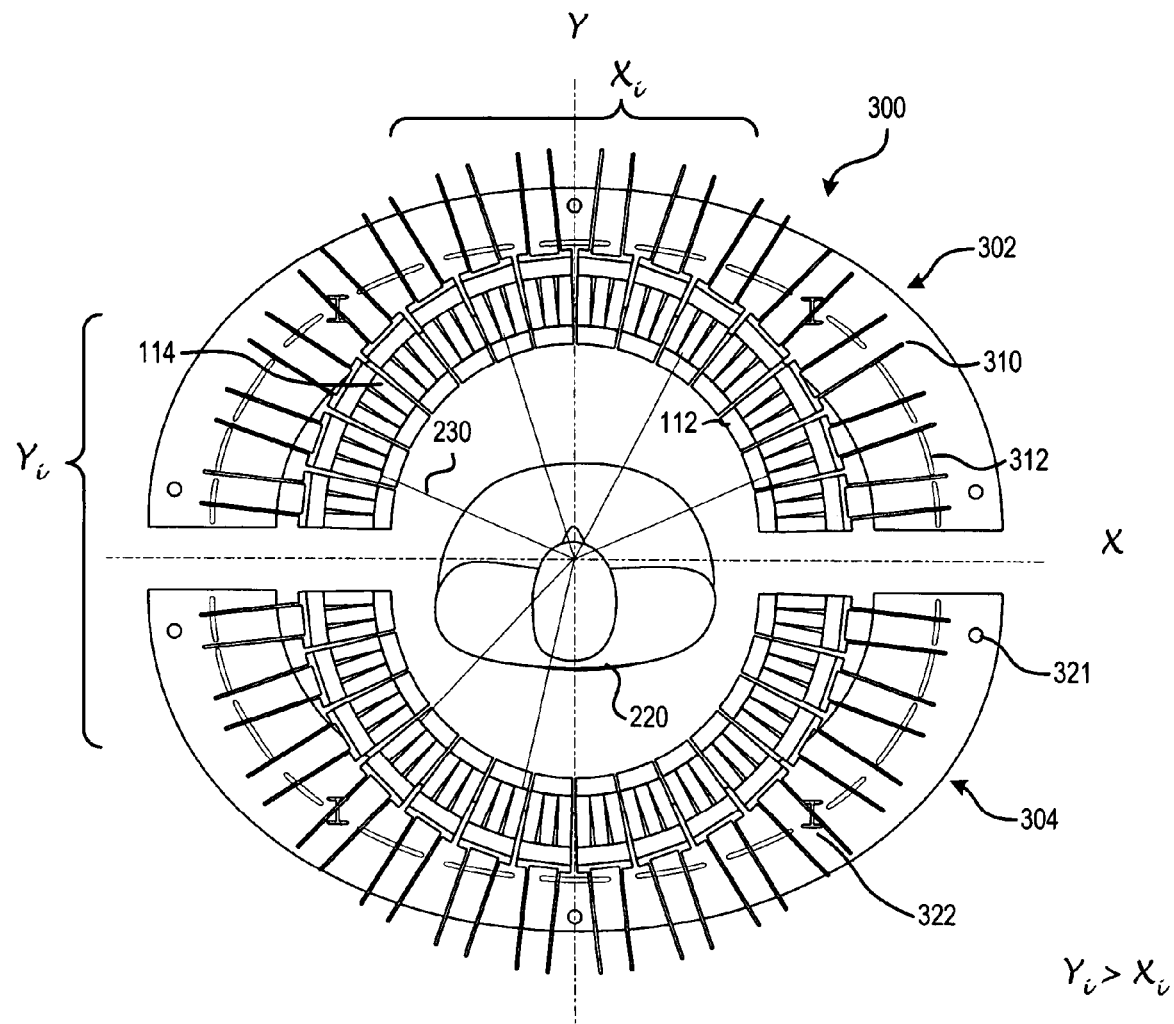
FIG. 4 is a diagram of a cross-sectional area of geometrically configurable detector array in accordance with another exemplary embodiment of the present invention.
Figure 5A:
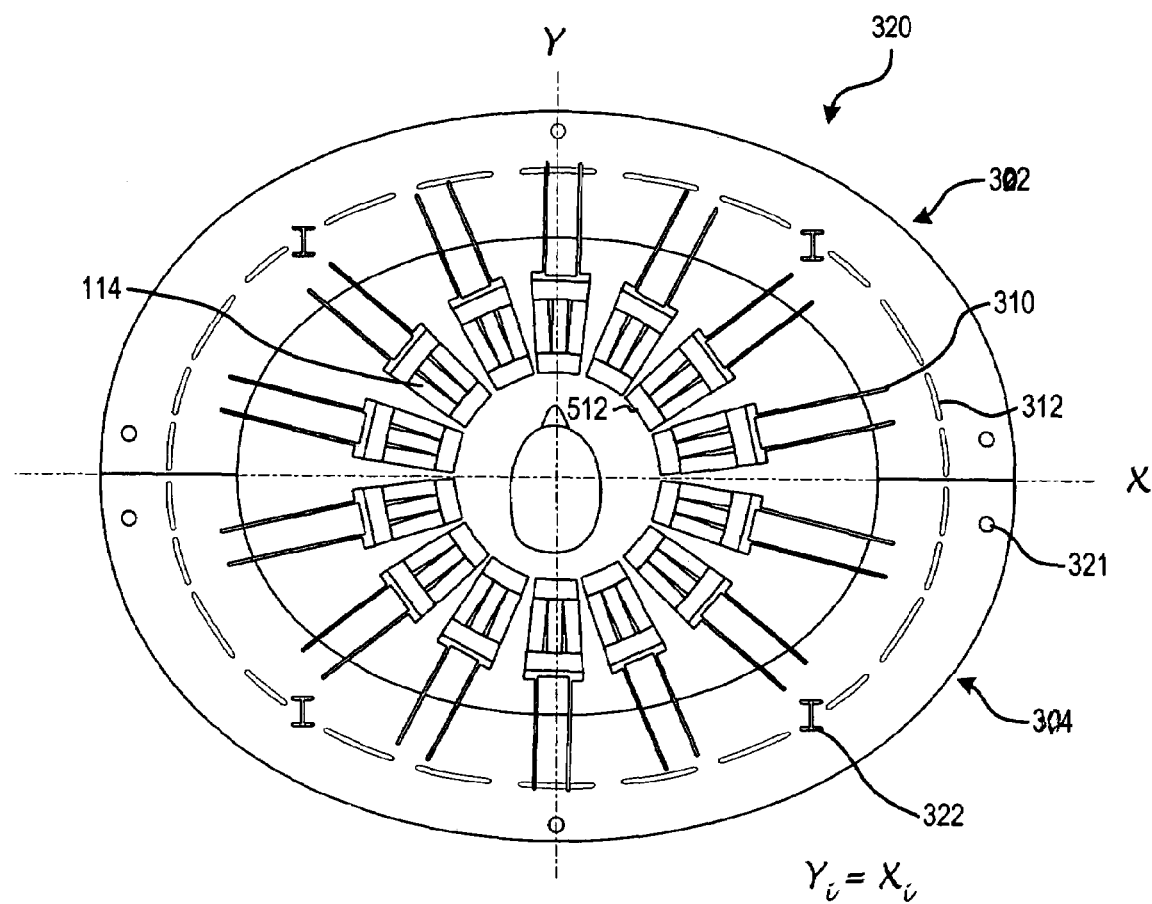
FIGS. 5A-5C are each diagrams of a cross-sectional area of a geometrically configurable detector FOV array support, separately geometrically configured for a portion of the patient's body.
Figure 5B:
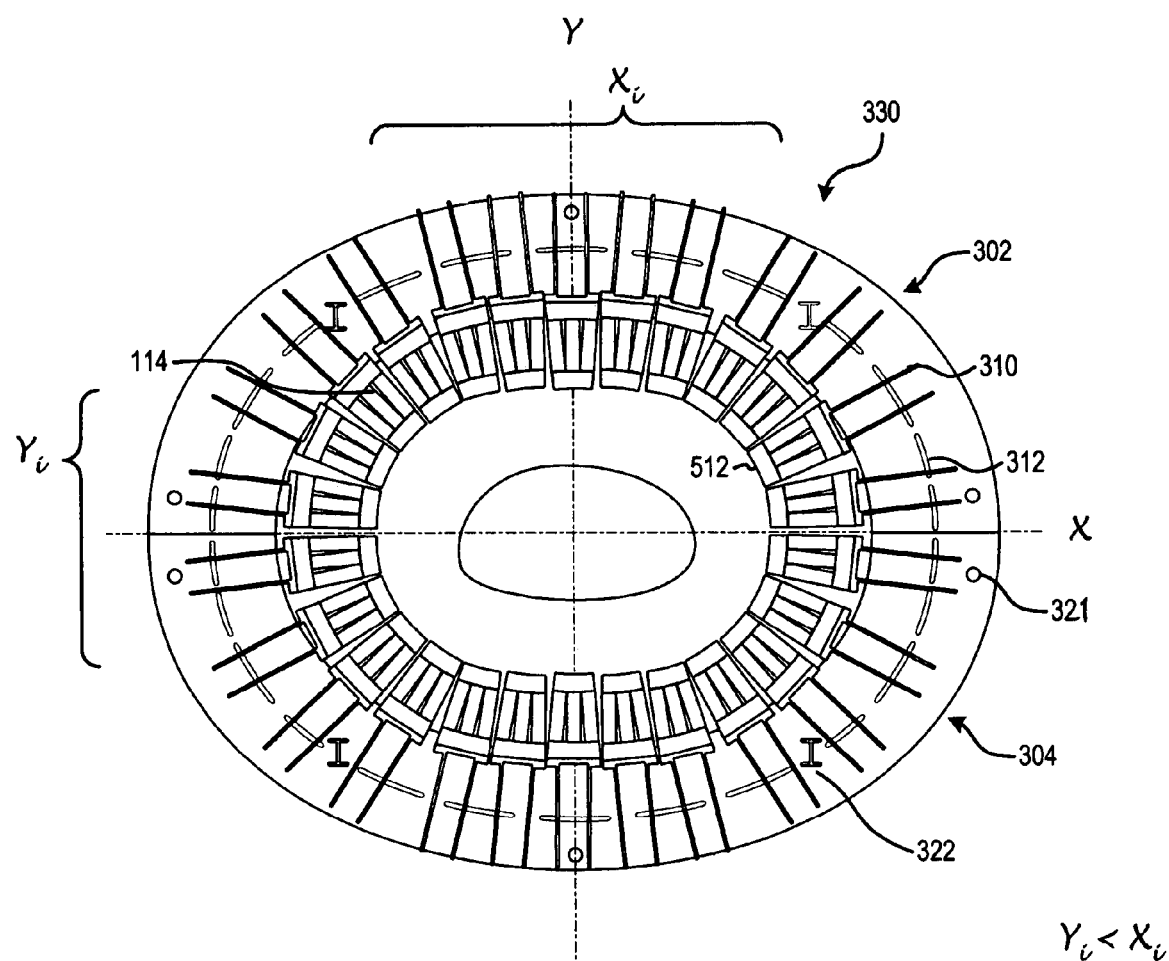
Figure 5C:
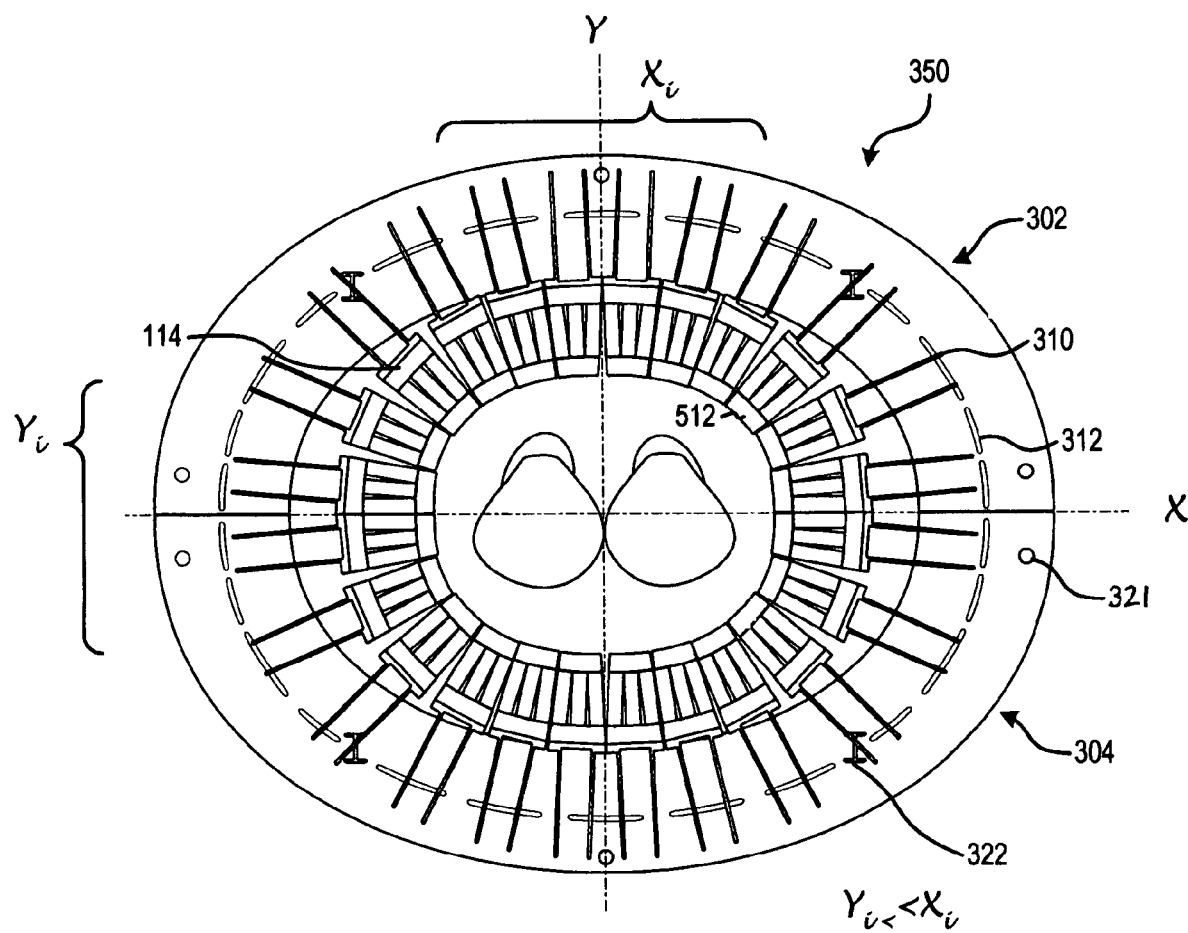

The present invention allows for detector configurations that simply were not possible in the prior art. One such configuration is the use of one crystal for capturing photons destined for multiple amplifiers. Here, each crystal 112 supports a linear array of three amplifiers 114. Alternatively, one crystal may be configured for supporting a matrix of 3×3 amplifiers or more. As will become apparent, the embodiments described herein of geometrically configurable PET detector arrays may serve to prove and optimize geometric configurations and orientations for product PET arrays. Thus, the product PET may well take advantage of extremely larger crystal structures, geometrically compliant with the geometry verified using the configurable arrays. In accordance with an exemplary embodiment of the present invention, FOV array 300 comprises two crystals, a substantially elliptical upper crystal for supporting the amplifiers secured to upper array support 302 and an identical substantially elliptical lower crystal for supporting the amplifiers secured to lower array support 304. Any number of crystals 112 may be formed in any suitable configuration, for example, FIGS. 3A, 3B and 4 show each semi-elliptical support as having fifteen crystals, FIG. 5A shows seven crystals, and FIG. 5B shows thirteen crystals, and FIG. 5C shows twelve crystals, with each crystal associated with a detector assembly 310. In the depicted example, array 300, while geometrically configurable, the geometric structure is essential round, as is known in the prior art. However, rather than being an inseparable circular detector array of the prior art, the present FOV array 300 is preferably two separate arrays, upper array support 302 and lower array support 304 which can be opened for a patient and then joined for the scan. Alternatively, upper array support 302 and lower array support 304 may be kept apart during the scan in order to accommodate patients who suffer from claustrophobia, obesity or simply larger individuals.

FIG. 4 is a diagram of a cross-sectional area of a geometrically configurable detector array in accordance with another exemplary embodiment of the present invention. Notice that all features of upper array support 302 and lower array support 304 are essential identical to those shown above with regard to FIG. 3A, but upper array support 302 has been dislodged from lower array support 304 for the scan. This is particularly important for patients who fear confined spaces, or those who do not physically fit in the scanning area of the PET.

As mentioned above, the present invention is intended to utilize multiple separately configurable cross-sectional FOV arrays, each corresponding with a cross-sectional area of a patient body separately geometrically configurable for a portion of the patient's body. FIGS. 5A-5C are each diagrams of a cross-sectional area of a geometrically configurable detector FOV array, 320, 330 and 350, respectively, each separately geometrically configured for a portion of the patient's body. FIG. 5A shows FOV array 320 geometrically in accordance with the shape of a patient head. FOV array 320 is arranged as a tight circle for optimal scanning. FIG. 5B is positioned further down the PET at a point adjacent to the patient's torso. FOV array 330 is arranged in an ellipse, for accommodating the patient's torso area. Finally, FIG. 5C is positioned still further down the PET adjacent to the patient's legs. FOV array 350 is also arranged in an ellipse, but much tighter than FOV array 330, for accommodating the narrower portion of the patient's legs.

Figure 6:
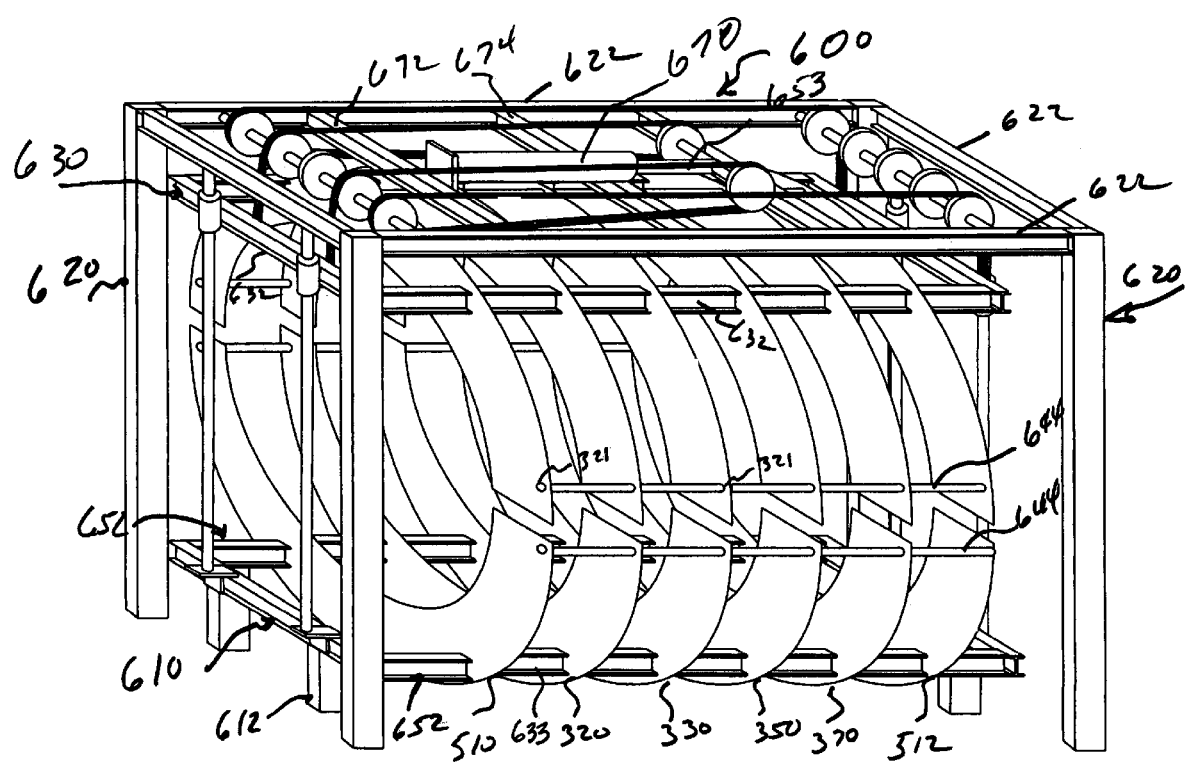
FIG. 6 is a diagram of PET gantry, including multiple FOV arrays each comprising an upper array support and a lower array support for separately configuring the cross-sectional area detector array in accordance with another exemplary embodiment of the present invention.

FIG. 6 is a diagram of PET gantry, including multiple FOV arrays 320, 330, 350 and 370, each comprising an upper array support and a lower array support for separately configuring the cross-sectional area detector array in accordance with another exemplary embodiment of the present invention. PET gantry 600 comprises a solid frame structure assembly placed on the ground (e.g., thick concrete capable to hold 40,000 lbs on eight point 25" square each). One frame structure 610 comprises floor supports 612 and lateral members 652 placed on four locations on the concrete that could hold about 20,000 lb. (5000 lb. each). A second frame structure comprises vertical supports 620 each connected to lateral supports 622 that are fixed to the ground on four locations on the concrete that could hold about 20,000 lb. (5,000 each), which is carrying the weight of the mobile structure 630, including lateral supports 632. Although four FOV arrays 320, 330, 350 and 370 are depicted, in practice any number may be used. The outer other semi ellipses (or semi rings) 510 and 512 may be FOV array, but in accordance with an exemplary embodiment of the present invention, outer supports 510 and 512 provide mechanical stability for the interior FOV arrays 320, 330, 350 and 370. The weight is carried by robust "I" beams 632, 633.

Each FOV arrays 320, 330, 350 and 370 carry the weight of the detector, photomultipliers, front-end electronics and cables supported by plurality of configurable detector assemblies 310 which are attached to the respective upper and lower supports of FOV arrays 320, 330, 350 and 370, using for example, fasteners such as U-bolts. The first support 510 and the last 512 are attached to long horizontal bars 644. These bars do not need to carry weight, their function is to keep a fixed distance between supports 510 and 512 and to guide adjustments of FOV arrays 320, 330, 350 and 370. Supports 510 and 512 provide a fixed structure for referencing to infer movements (small angles) to supports 510 and 512, and others, up to one before 512 as it is shown by FOV arrays 320, 330, 350 and 370. The position of supports 510 and 512, is rigidly attached to the "I" beams 632, 633, e.g., by 90 degree angle brackets. This assembly provides a rigid structure that could be used as reference for adjusting the position of the detector element with respect to the axis of the barrel. Small adjustment of the orientation of the detector could be made by fixing FOV arrays 320, 330, 350 and 370 to different positions along bars 644, which pass through holes 321. The detector can also have a different orientation (e.g., $A_r$ in FIG. 3B) in the other direction (or degree of movement, e.g., $A_\theta$ in FIG. 3B) by moving upper array supports 302 around the two hinges 316 and 319 at both ends with the protruding arms of mounting support 314.

The crystal (or any type of detector), photomultipliers, and cables are attached to the upper array supports which is attached to mounting support 314 by strong hinges 316 and 319 which give the flexibility to change the alignment (orientation) of the detector assembly 310 with respect to the radius of the barrel ($A_F$). Each metal tube 315 or 318 (square or round) of mounting support 314 is attached to FOV arrays 320, 330, 350 and 370 by, for example, three U-bolts that provide maximum reliability (safety to the patient) for holding any type of detector. Mounting support 314, and metal tubes 315 and 318, can hold a detector assembly block (e.g., PMT, cables, etc.) that can be separated from adjacent blocks, or can be one support to hold a single block of half ring detector. Mounting support 314, and metal tubes 315 and 318, and its associated detector assembly 310 can be moved closer or at a longer distance from the center of the barrel allowing to build a barrel detector which is a cylinder, an ellipse, a combination of the two shapes (e.g., cylindrical for the head and elliptical for the torso) or to implement a shape that best surrounds the patient's body.

Lower array support 304 comprises two structures, one rigid which is fixed to the concrete (comprising vertical supports 612 and upper lateral supports 622) and an upper mobile structure (which provides a vertical movement) comprising lateral supports 632 carrying the weight of upper support 302 from each of FOV arrays 320, 330, 350 and 370 as well as any other semi ellipse (or semi ring) supports until outer supports 510 and 512. The weight is carried by two robust "I" beams 632.

The upper mobile structure (half barrel) is lifted by an hydraulic oil system (see cylinder 670, that is pulling the chain 653 which is pulling (when the piston is extended) two chains anchored to the transverses 672 and 674. A security system, which can be released only manually through a pneumatic system, by the same person who is activating the lowering of the lift by gravity, is finding a vertical stop every about 7 inches, which is an impediment to the upper half barrel to go further down.

The gantry systems of the present invention provide the advantages of flexibility to accommodate detectors of different type, weight, shape, and distance from the patient (or center axial of the barrel), and the advantage of cost-effectiveness. No other known scanner systems allow splitting of the detector barrel into two sections and lifting of the upper part. All other detector barrels are in a ring (circular, octagonal, etc.), and some have the possibility to adjust the distance of some block of detector from the patient. None has a construction that allows expanding the entire field of view, e.g., from a few cm to more than one meter. The design of the present gantry allows assembly of two half-barrel detectors (upper and lower) in only two pieces or in several blocks of detectors covering a certain portion of space in radius and in length (e.g., one quarter of detector, ⅛, etc., in radius, and 20 cm, 40 cm, 60 cm, etc. in length). The detector can be expanded starting from a PET with a geometry identical to existing PET made of a circular ring with 16 cm FOV, to a detector of any shape and longer than one meter). The support FOV arrays 320, 330, 350 and 370 as well as any other semi ellipse (or semi ring) supports including outer supports 510 and 512 (additional supports not shown) allow to create no gap, a small gap or a longer gap between detector rings for CT or other objects. The system also allows for adjusting the orientation of the detector toward the patient (e.g., 90 degrees).

Preferably, each piece should weight less than about 120 lb. (with the exception of the transverse 674 that has the cylinder and piston of the hydraulic system), so that the entire gantry could be assembled and disassembled by a single person. Because of the rugged, however, reliable construction, the gantry can be assembled on a truck, on a hospital or imaging center.

Figure 7A:
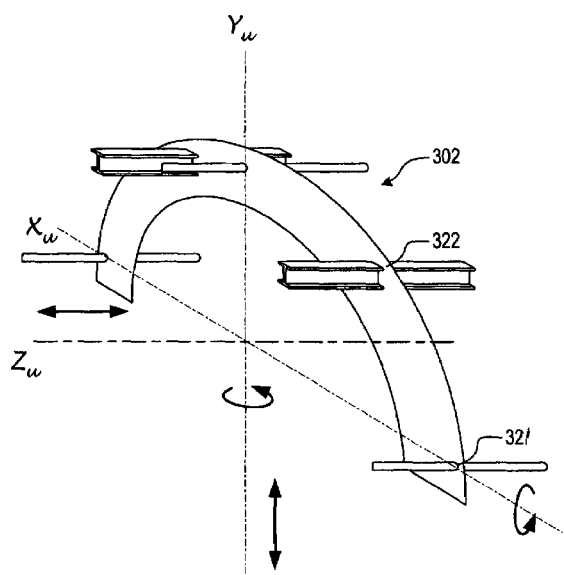
FIGS. 7A and B are perspective view illustrations of an upper array support and a lower array support, respectively, depicting the four degrees of freedom for adjusting each of the array supports and cooperating detectors in accordance with an exemplary embodiment of the invention.
Figure 7B:
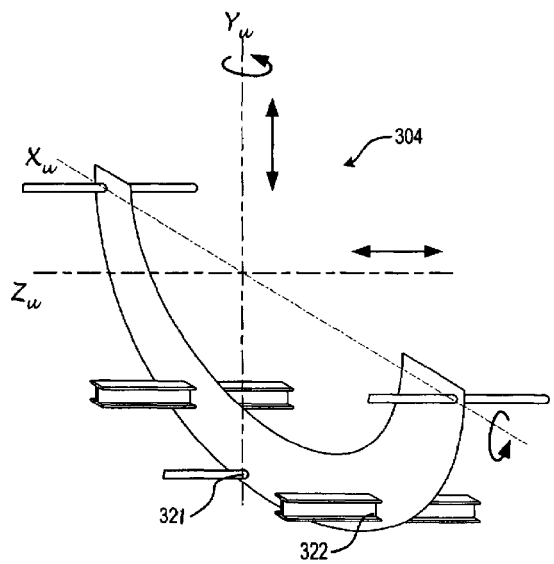

FIGS. 7A and 7B depict the four degrees of freedom for adjusting each of the upper and lower array supports and cooperating detectors.

EXAMPLE

An exemplary gantry as shown in FIG. 6, which accommodates detectors of different type and shape, was built in approximately one month, working part time and spending only $5,000 in material. FIGS. 3A, 3B, 4, and 5 show the construction of the support of the detector. The rectangular hole in the two semi-arcs is accommodating the I beam of the gantry and is where the weight of the detector is laying. The six round holes (three on the top semi arc and three on the bottom semi arc) are used to accommodate a tube which is solid to the gantry and has a clamp at each semi arc that provides a rigid position of the arc with respect to the gantry.

An advantage of this construction is that it will help to increase the flexibility in using different types of detector geometries and materials and it lowers the cost of the overall PET because of its simple design. The construction is safe for the patient: e.g., it can accommodate 3-cm thick BGO or LSO detectors assembled in many blocks, or two half barrel, 7-cm thick NaI(TI) detectors. It allows for construction of a circular detector for head and torso or any elliptical geometry for any section of the body, and can be used for prototyping as well as for final commercial products. The upper section of the gantry was tested to lift over 7000 pounds (the estimated weight to be lifted will be 1500 pounds).

The upper half of the exemplary detector is lifted by an oil based hydraulic system. The lowering of the upper part of the detector is by gravity and is regulated by an oil fluid regulator. The safety of the weight of the upper section of the detector is based on gravity, it is always in place and its deactivation is controlled by a pneumatic system. The operator will deactivate the protection on lowering the detector when the patient is in a safe position by pressing a button and keeping his hand on the button continuously. If the button is released, the safety system is reactivated; the upper half of the detector in this condition cannot step down more than 7" before finding a mechanical stop. A safety mechanical stop also prevents the upper detector from going any lower than 36" from ground. Four telescoping aluminum guides assure alignment of the upper with the lower detector. The overall detector gantry can be disassembled and re-assembled in one day by a single person with the exception of one transverse member, on which is mounted the hydraulic piston and cylinder that together weigh about 300 pounds.

The above mechanical construction allows the accommodation of any off-the-shelf detector, and the placing of them at a selectable distance from the patient. The advantage of the proposed construction is that it is adaptable to accommodate the circular 16-cm FOV detectors of the PET and PET/CT currently operating in hospitals, as well as longer detectors up to 180 cm. The lower cost of the proposed gantry and the possibility of lifting the upper half allows an economical implementation of PET as well as solving the problem for claustrophobic people when the FOV is increased. This offers the possibility to test some commercially available detectors with the 3D-Flow electronics implemented in FPGA using a phantom made of water with a long life radioactive source.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A gantry for configuring a positron emission tomography (PET) apparatus comprising:
 a frame assembly having a longitudinal axis; and
 a first detector support ring coupled with the frame assembly, the first detector support ring defining a scanning area for scanning a patient and comprising a semi-elliptical upper portion and a semi-elliptical lower portion, the upper portion moveable with respect to the lower portion in a direction approximately perpendicular to the longitudinal axis;
 wherein said upper and lower portions are each configured to adjustably support at least one detector assembly,
 wherein the frame assembly comprises a first frame structure for supporting the upper portion of the first detector support ring and a second frame structure for supporting the lower portion of the first detector support ring, and
 wherein the upper portion of the first detector support ring is suspended from the first frame structure and moveable in a vertical direction with respect to the lower portion of the first detector support ring.

2. The gantry system of claim 1, wherein the first frame structure comprises a hydraulic system for moving the first detector support ring.

3. A gantry, comprising:
 a frame assembly having a longitudinal axis and comprising an upper frame structure and a second lower frame structure;
 a plurality of planar upper array supports adjustably coupled to the upper frame structure and arranged along the longitudinal axis, each of said plurality of upper array supports adjustably securing an array of detector assemblies, wherein each of said plurality of upper array supports is adjustable with respect to each other in a direction parallel to the longitudinal axis of the frame assembly; and
 a plurality of planar lower array supports adjustably coupled to the lower frame structure and arranged along the longitudinal axis, each of said plurality of lower array supports adjustably securing an array of detector assemblies, wherein each of said plurality of lower array supports corresponds to one of the plurality of upper array supports and is adjustable in a direction parallel to the longitudinal axis of the frame assembly;
 wherein said plurality of upper array supports is suspended from the upper frame structure and adjustable in a direction substantially perpendicular to the longitudinal axis of the frame assembly, and
 wherein adjustment of the plurality of upper array supports away from the plurality of lower array supports increases a dimension of a scanning area defined by the arrays of detector assemblies secured to the plurality of upper and lower array supports.

* * * * *